July 7, 1964 C. FISCHER Plant Pat. 2,416
GLADIOLUS PLANT
Filed May 23, 1963
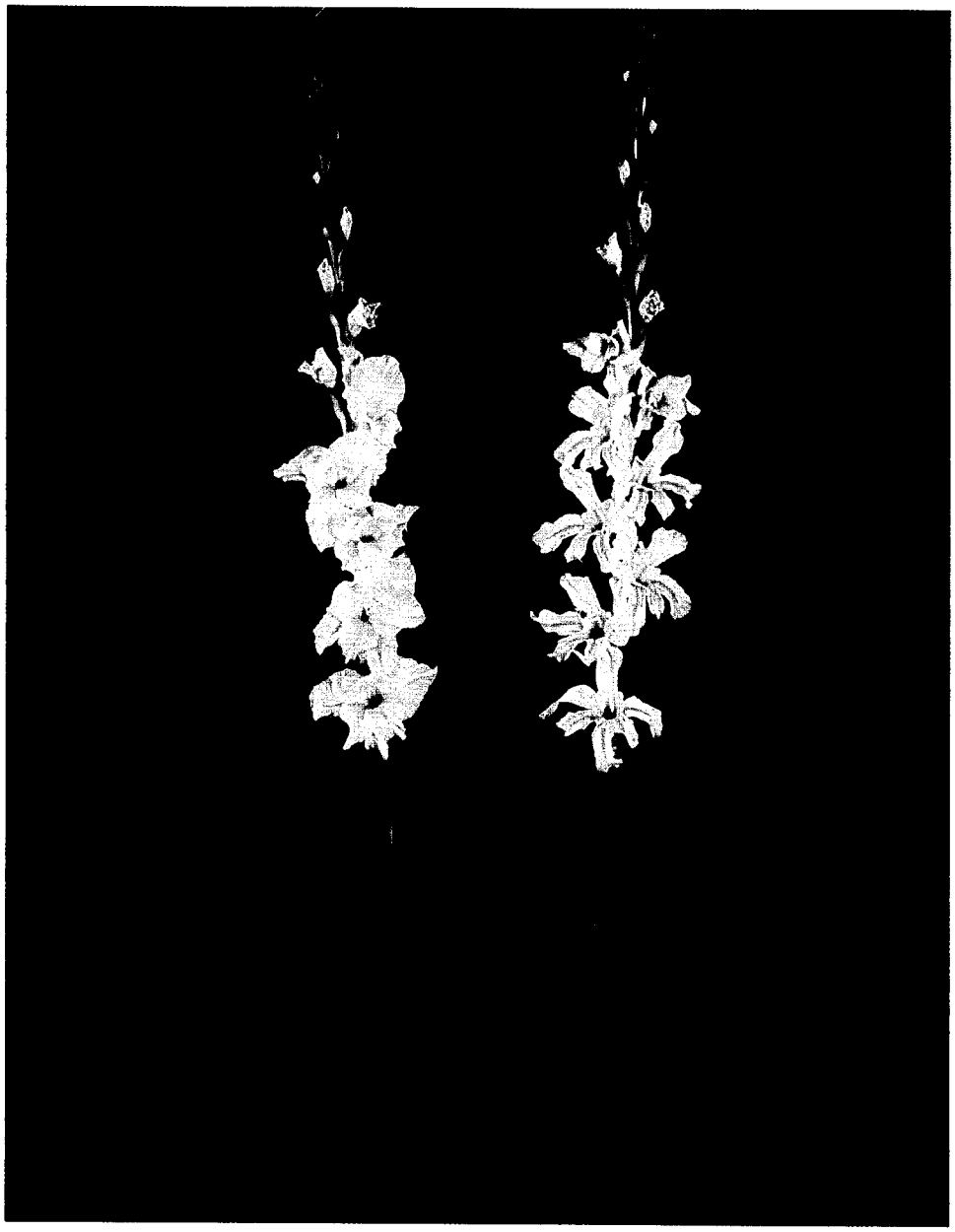
Inventor.
Carl Fischer
By: Robb & Robb
Attorneys.

United States Patent Office

Plant Pat. 2,416
Patented July 7, 1964

2,416
GLADIOLUS PLANT

Carl Fischer, St. Charles, Minn., assignor to Imperial Flowers Limited, Leamington, Ontario, Canada, a corporation of Canada Filed May 23, 1963, Ser. No. 282,824
1 Claim. (Cl. Plt.—85)

The present invention relates to a new and distinct variety of gladiolus plant which was originated by me by crossing two gladiolus varieties whose identities are presently unknown by virtue of the fact that my breeding records of this cross and the plant labels were lost during the breeding and testing operations.

As the result of this breeding, I have produced a new and improved gladiolus variety, as evidenced by the following unique combination of characteristics which are outstanding therein and which distinguish it from its parents, as well as from all other varieties of which I am aware:

(1) A robust plant habit;
(2) An unusual floret form;
(3) Good flower head length;
(4) A distinctive and attractive Aureolin general color tonality of the flowers, with a Scarlet to Blood Red blotch and a Blood Red midrib on the lower petals of the narrower florets; and
(5) The production of strong bulbs.

My new variety does not resemble any other variety heretofore known, so far as I am aware, and is the only variety known to me which has the unique floret form of both broad and narrow florets, with the broad florets being ruffled, recurved and butterfly shaped, and the narrow florets being recurved, twisted and laciniated.

Asexual reproduction of my new variety by cormels through several generations, as performed by me at St. Charles, Minnesota, shows the foregoing characteristics and distinctions come true to form and are established and transmitted through succeeding propagations.

The accompanying drawing shows two typical plants, including foliage and flowers of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations from cormels.

*Plant*

Growth: Extremely vigorous; average propagator.

Blooming habit: Mid-season bloomer in the Northern latitudes of the United States; comes into bloom from the planting of large bulbs in about 85 days.

Stems: strong; straight.

*Diameter at base.*—About ½ inch.

*Color (at base).*—White.

Foliage: Healthy; very leathery; broad; drooping; leaves average about 2¼ inches wides and attain a height of about 38 inches; leaves separate easily from stem, thus making it easy to cut. Color—Dark green.

Disease resistance: Especially resistant to all of the ordinary diseases to which gladiolus varieties are normally subject in the Minnesota area, as determined by comparison with other varieties grown in my fields near St. Charles, Minnesota.

Corms (bulbs): Corms from mature bulbs are round and somewhat flat, with younger corms being higher crowned; husks cover bulbs well and are straw color with a reddish tint. Color of flesh—Buttercup Yellow, Plate 5/2 in mature corms, and Buttercup Yellow, Plate 5/1 in younger corms.

*Flower*

Spike: Blossom spike ranges from about 60 inches to 66 inches tall, with flower head ranging from about 30 inches to 35 inches long; bears 24 or 25 buds, with 6 to 8 buds open at one time.

Bud:

*Size.*—About 2 inches long when opening.

*Opening.*—Opens well; 6 or 7 buds show color at one time.

Flower:

*Arrangement.*—Florets are informally arranged on the stem.

*Size.*—Individual florets range from broad to narrow and average about 5 inches in diameter.

*Form.*—Broad florets—ruffled; recurved; butterfly shaped. Narrow florets—recurved; twisted; laciniated.

*Keeping qualities.*—Keeps well.

Petals:

*Shape.*—Broad type petals—Ruffled; recurved and butterfly shaped. Narrow type petals—recurved; twisted and laciniated.

*Size.*—Broad type florets—average about 2¼ inches in width in case of upper petals with lip petals averaging about 1½ inches wide. Narrow type florets—average about ¾ inches wide in case of upper petals with lip petals averaging ⅜ inches wide.

*Aspect.*—Heavy substance; ruffled and corrugated surface.

*Fragrance.*—None.

*Color.*—Basically Aureolin, Plate 3/2, with blotch ranging between Scarlet, Plate 19/1 and Scarlet, Plate 19; broad line of blotch on broad florets is Blood Red, Plate 820, and midrib on the lower petals of the narrow florets is also Blood Red, Plate 820.

*Reproductive Organs*

Stamens: Color—yellow.

Pistils: Color—yellow.

Pollen: Sparse.

I claim:

A new and distinct variety of gladiolus plant, substantially as herein shown and described, characterized particularly as to novelty by the unique combination of a robust plant habit, an unusual and distinct floret form ranging from broad to narrow, good flower head length, a distinctive and attractive Aureolin general color tonality of the flowers, said flowers having blotches of Scarlet, with a broad Blood Red blotch line on the broad florets and a Blood Red midrib on the lower petals of the narrow florets, and a habit of producing strong bulbs.

No references cited.